United States Patent [19]

Gorokhovsky et al.

[11] 4,362,152

[45] Dec. 7, 1982

[54] ERECTOR

[76] Inventors: Veniamin Gorokhovsky, 1231 N. Genesee Ave., #7, Los Angeles, Calif. 90046; Grigory Fradkin, 1230 N. Sweetzer Ave., #313, Los Angeles, Calif. 90069

[21] Appl. No.: 165,248

[22] Filed: Jul. 2, 1980

[51] Int. Cl.$^3$ ............................................. A61F 5/42
[52] U.S. Cl. ..................................................... 128/79
[58] Field of Search ......................................... 128/79

[56] References Cited

U.S. PATENT DOCUMENTS 3,511,230   5/1970   Strong ................................. 128/79

FOREIGN PATENT DOCUMENTS 178044   2/1966   U.S.S.R. ................................ 128/79
589978   2/1978   U.S.S.R. ................................ 128/79

*Primary Examiner*—Kyle L. Howell
*Assistant Examiner*—Nancy A. B. Swisher
*Attorney, Agent, or Firm*—Peter J. Groom

[57] ABSTRACT

A prosthetic erector for remedying problems of impotency in males is disclosed. The erector has a pair of substantially rigid rods, the rods being encased within a common elastic encasement in a side-by-side relation. The rods have at a first end, a yoke defined by first and second arms forming a pair of spaced apart, generally hooked-shaped arcuate arms adapted for encircling the glans of the penis around and in abutment with the penis corona. Securement means are provided at the second end of the rod for securing the erector to the penis. The securement means includes an elastomeric tube adapted for securement around the scrotum at the root of the penis. The rods have a bend located at a station about one-third the length of the rod away from the first end, the bend for contacting the penis superficial dorsal vein for applying pressure thereto. The second end of each rod has a bend surrounded by an enlarged encasement for contacting and applying pressure to the penis superficial dorsal vein and corpora cavernosa. The securement means is capable of stretching and retracting in response to corresponding changes in penile erection, and expansion of the glans causes the arms of the yoke to rotate relatively further apart causing the second ends of the rods to rotate relatively closer together stretching the securement means thereby causing the second ends of the rods to exert increasing pressure on the dorsal vein and corpora cavernosa, without causing pressure on the arterial vessels and corpus cavernosum urethra.

31 Claims, 14 Drawing Figures

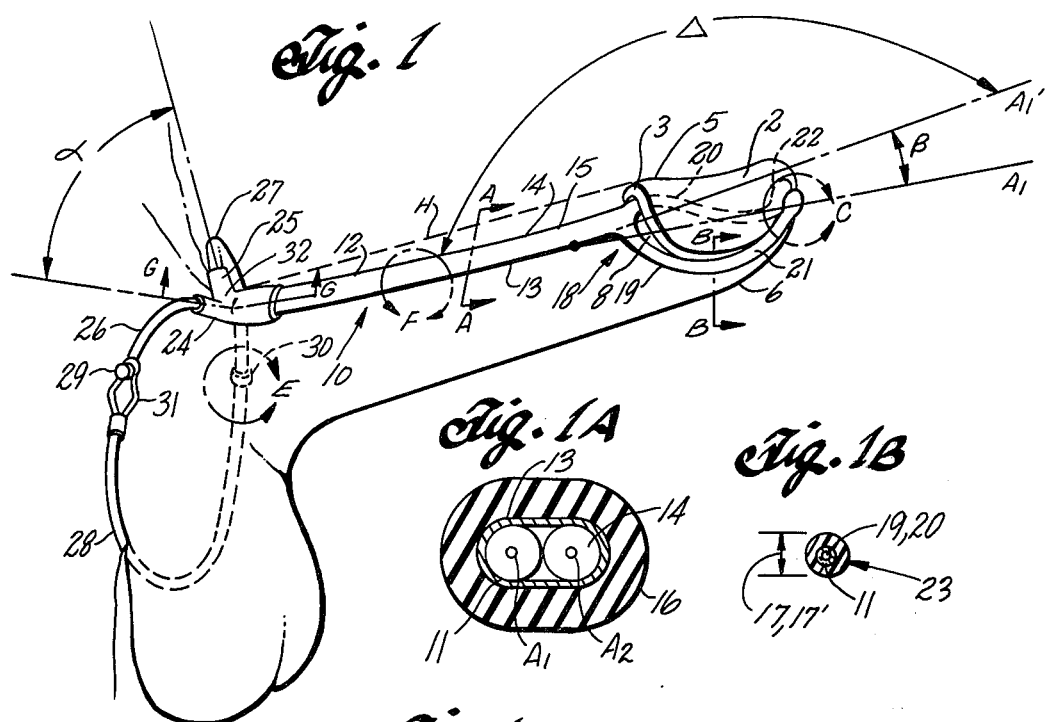

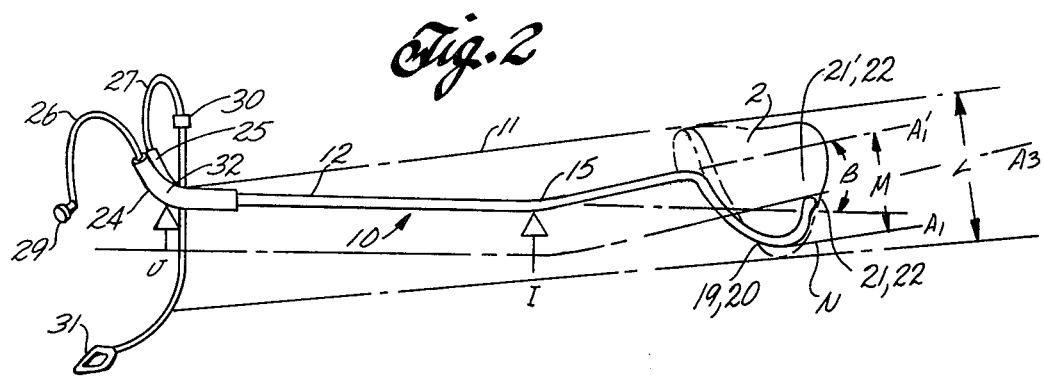
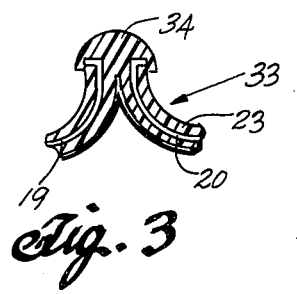
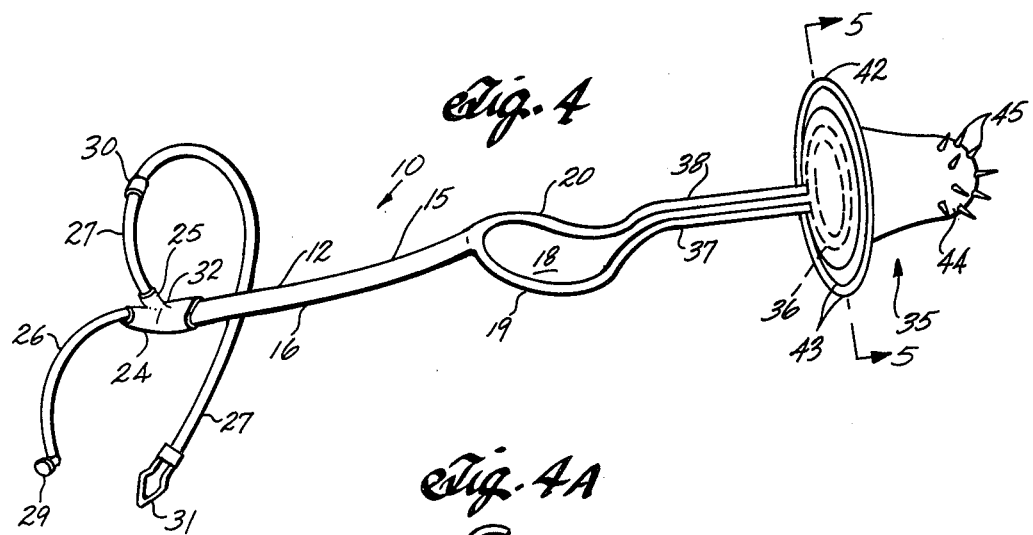
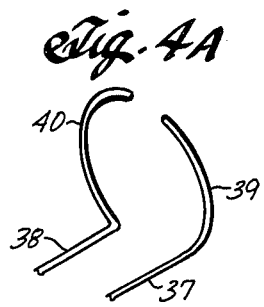

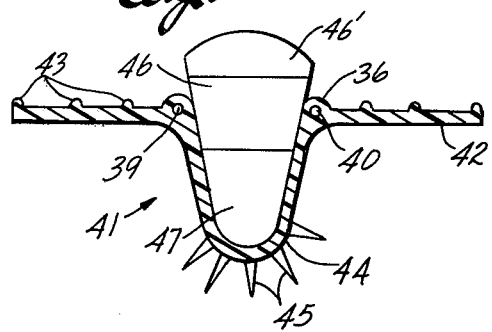
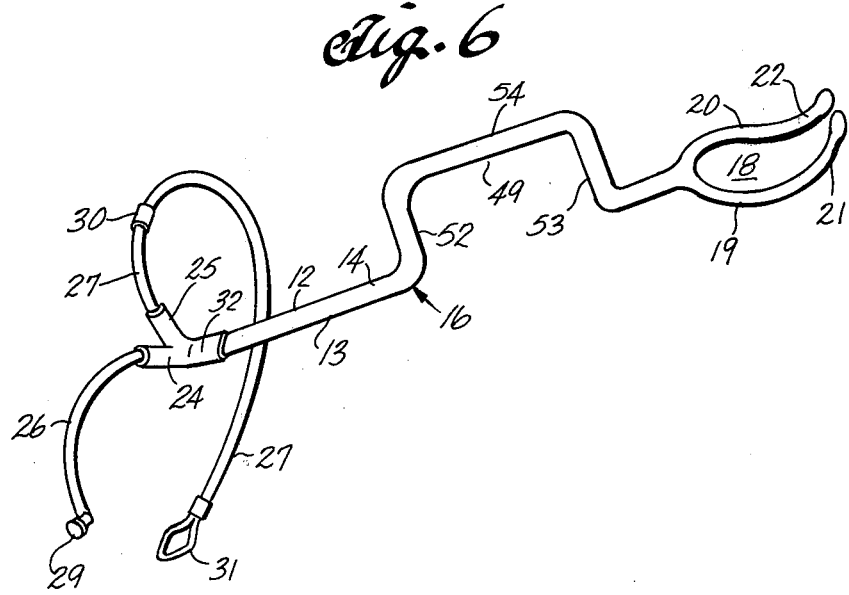

ERECTOR

BACKGROUND OF THE INVENTION

This invention relates generally to a prosthetic device used in the treatment of male impotency by stimulation and the maintaining of penile erection.

Male impotency can be traced to a wide range of medical, mental, physical and physiological problems. For example, endocrinological disorders such as diabetes are very common causes of male impotency. For example, it has been found that about 50% of the male patients suffering from diabetes also develop impotency. Deficiencies in thyroid functions are also responsible for male impotency. Other factors such as reduced arterial flow, the use of drugs, alcohol and narcotics, anatomical problems, as well as postsurgical manifestations, give rise to impotency.

Prosthetic devices for remedying male impotency are well known. One class of device is the type that is implanted within the penis corpora cavernosa. These devices may be of the type that are permanently rigid or controllably inflatable.

An inflatable-type device is described by Robert E. Buuck in U.S. Pat. No. 3,954,102 entitled, Penile Erection System and Methods of Implanting and Using Same. Buuck describes a pair of expandable, elastomeric cylinders which are implanted in the penis corpora cavernosa. An elastomeric tube that functions as a pump is placed between a fluid reservoir and the expandable cylinders. The pump is used to pump fluid from the the reservoir into the cylinders to cause erection and a bypass check valve is provided such that deflation is accomplished by actuating the bypass valve.

Surgical procedures for accomplishing the implantation of the described prosthetic devices have taken on the order of 4 hours. In addition to subjecting the patient to the surgical procedure, there is potential of post-operative infection necessitating yet further surgery and related medical treatment.

Other devices for remedying impotence are of the type that are exteriorly applied for either simulating or maintaining penile erection. For example, Bagby in U.S. Pat. No. 3,794,020 describes an anatomical device for attachment about the root of the penis. The purpose of such devices is to constrict the return flow of veinal blood and thus maintain the penis in the erected state. The device, however, causes an uncontrolled pressure on the superficial dorsal vein about the root of the penis strangulating it which, due to the repeated, continual use of the device, may lead to a breakdown of the connective tissues of the corpora cavernosa.

Another externally-applied device is described by Line in U.S. Pat. No. 3,930,007. The device has a ring-like base having a diameter slightly larger than the root of the penis. A rigid support column is secured at one end in a substantially perpendicular orientation to the ring-like base. A collar is connected to the other end of the rigid support column and is adapted for telescopically receiving the glans of the penis.

The ring-like base is characterized in that it may rotate, and the rigid support column and collar will be misoriented, potentially leading to injuries during use of the device. Additionally, the collar has a planar, circular shape so that the collar does not conform to the shape of the corona of the glans of the penis. Consequently, it cannot provide proper engagement with the glans.

Yet another device for treating impotency is described in Russian Pat. No. 178,044 by Ploticher, S. A. et al. The device described comprises retaining rods contained within a common case. The rods have at one end a planar supporting ring for securing the device to the penis and at the other end yoke pieces that conform to the shape of the female organ. The rods, however, do not control the flow of veinal blood in the dorsal vein and the corpora cavernosa in order to control the level of penile erection.

The extremities of the yoke, however, abut at a single point of contact and in the corona sulcus under the glans. The extremeties of the yoke are characterized in that they have a tendency of sliding against and relative to each other resulting in one extremity projecting beyond the other. The extremeties therefore are capable of contacting the inner vaginal wall in a manner leading to potential serious injury to the female.

SUMMARY OF THE INVENTION

The problems and deficiencies in the prior art are overcome with the embodiment of the present invention and provide a man with the capability of performing a natural physiological sexual act with insufficient or totally absent erection.

An embodiment of the present invention is a prosthetic device for remedying problems of impotency in males. The erector has a pair of rods, each rod having first and second ends. A yoke is formed by the first ends of the rods. The yoke has first and second arms that form a pair of spaced apart, generally hook-shaped arcuate arms that are adapted for encircling the glans of the penis around and in abutment with the corona sulcus. Attachment of the erector to the user is provided by an elastomeric tube secured to a second end of one of the rods and adapted for attachment, around the base of the scrotum, to a corresponding second end of the other rod.

The rods have a first bend defined by a predetermined included angle. The first bend is located at a station about one-third the length of the rod away from the first end of the rod. The rod, at the first bend, contacts the penis superficial dorsal vein for applying pressure thereto for controlling the flow of veinal flow in the dorsal vein.

As a feature of the invention, the elongated rods are substantially rigid and are encased within a common elastic sleeve. The rods are in general side-by-side relation, the rods being held in such relation by a thin filament thread wrapped around both rods thus providing the capability of rotation of the rods about an axis thereof through a predetermined angle.

As another feature of the invention, each rod at the second end thereof has a second bend, said second bends being angularly displaced from each other at a predetermined angle. The rods, at the second bend, have an enlarged encasement for contacting and applying pressure thereby to the superficial dorsal vein at the root of the penis. The second ends of the rods form a pair of supporting arc portions that conform to the shape of the pubic muscles.

As yet another feature of the invention, the elastomeric tube is capable of stretching and retracting in response to corresponding changes in erection of the penis such that a corresponding expansion of the glans causes the arms of the yoke to rotate relatively further apart causing the supporting arc portions of the rods to rotate relatively closer together stretching thereby the elastomeric tube causing the rods at the second bends and the elastomeric tube to exert relatively increasing pressure on the dorsal vein and corpora cavernosa without causing pressure on arterial vessels and corpora cavernosum urethra.

Preferably, the erector includes defloration means comprising a substantially spherical probe mounted to the erector at the extremity of the yoke arms.

Preferably, the erector includes a pair of compensators that are coupled to the yoke's first and second arms. The compensators are adapted for mounting thereon a resilient hollow thimble-shaped probe having a plurality of resilient projections at the outer surface of the probe. The compensators also compensate for the difference between the length of the penis and the depth of the vagina. The thimble-shaped probe is for imitating the glans of the penis.

Preferably, the invention includes a plug adapted for providing a water-tight seal at the open end of the probe.

BRIEF DESCRIPTION OF THE DRAWINGS

FIG. 1 is a perspective view of the erector according to the invention;

FIG. 1B is a cross-sectional view taken along lines B—B of FIG. 1;

FIG. 1C is a cross-sectional view taken along lines C—C of FIG. 1;

FIG. 1D is a view of the penis glans and erector yoke taken along axis $A_1$ of FIG. 1;

FIG. 1E is a partial cross-sectional view taken along lines E—E of FIG. 1;

FIG. 1F is a partial cross-sectional view taken along line F of FIG. 1;

FIG. 1G is a partial cross-sectional view taken along lines G—G of FIG. 1;

FIG. 2 is a front elevation view of the erector of FIG. 1;

FIG. 3 is a partial cross-sectional view of a defloration probe intended for use on the erector of FIG. 1;

FIG. 4 is an erector according to the invention including a thimble-shaped probe 41;

FIG. 4A is an exploded view of a pair of compensators used in the erector of FIG. 4;

FIG. 5 is a partial cross-sectional view taken along lines 5—5 of FIG. 4; and

FIG. 6 is a perspective view of an alternate embodiment of the erector of FIG. 1.

DETAILED DESCRIPTION

Referring now to FIG. 1, there is shown in perspective view an erector of a form adapted to incorporate the teachings of this invention. The erector 10 has an initially stressed column 12 that forms a central portion of the erector. The column 12 comprises a pair of rods 13 and 14 (see FIG. 1A) that are oriented in side-by-side relation and are held in proximity to each other by a thin filament thread 11 wrapped about the rods preferably in a helical fashion (see FIG. 1F). The rods 13 and 14 are encased in an electric sleeve 16 and are capable of rotation about an axis thereof within the sleeve. Preferably, the rods 13 and 14 are formed of substantially rigid spring wire having a circular cross section. Preferably, the sleeve 16 is formed from non-toxic elastic material such as rubber or latex.

A yoke 18 is located at one end of the column 12. The yoke 18 is formed by a pair of complementary spaced apart, generally hooked-shaped arcuate arms 19 and 20 that form one extremity of the respective rods 13 and 14. The arms 19 and 20 are embedded in an elastic sleeve 23 (see FIG. 1B) such as rubber or latex. The extremities 21 and 22 of the respective arms 19 and 20 are normally in side-by-side abutting relation (as best shown in FIG. 1D). The sleeve 23 about the tips 21' and 22' of extremities 21 and 22 respectively is generally pear-shaped and being somewhat enlarged relative to the sleeve for the remainder of the arms (see FIG. 1C).

The second ends 24 and 25 of the rods 13 and 14 respectively, have a generally upwardly-pointing bend (as viewed in FIG. 1), the second ends being angularly displaced through an angle $\alpha$. Preferably the angle $\alpha$ is about 90°.

The second ends 24 and 25 have (as viewed in FIG. 1) upwardly and outwardly pointing supporting arc portions 26 and 27, respectively. The supporting arc portions 26 and 27 are shaped to conform to the contour of the upper portion of a male's pubic muscles.

An elastomeric tube 28, preferably hollow, is clamped to the supporting arc portion 27 by means of a clamping ring 30.

The elastomeric tube 28 is detachably engageable with the supporting arc portion 26 by means of the locking action of a closed loop ring 31 secured to the free end of the tube 28 and a mushroom-shaped button 29 secured to the extremity of supporting arc portion 26. It will be appreciated that the choice of location of the tube 28 and supporting arc portion 26 for securement at the right side of the scrotum, as shown in FIG. 1, is arbitrary and selectable for the convenience of the user.

The clamping ring 30, as described below, provides means for adjusting the length of the elastomeric tube to suit the convenience of the user. Clamping ring 30, as better seen in FIG. 1E, is in the general shape of a cylindrical ring having a frusto-conical interior wall portion 60 coaxial with an interior cylindrical wall portion 62. Supporting arc portion 27 has an enlarged tip 64 that is capable of being positioned at selected stations within the hollow elastomeric tube 28. The interior cylindrical wall portion 62 has a diameter smaller than the elastomeric tube's outer circumference 66 as determined at the point at which the tube extends over the enlarged tip 64.

For adjusting the length of an unstressed elastomeric tube, as measured between enlarged tip 64 and closed loop ring 31, the clamping ring 30 is moved away from the enlarged tip 64 towards encasement 32 permitting the elastomeric tube 28 to be moved on the supporting arc portion 26. At the station providing the desired elastomeric tube length, the clamping ring 30 is moved towards the enlarged tip 64 until the action of the conical wall portion 60 causes the elastomeric tube 28 to be wedged against and thereby locked to the enlarged tip 64.

The rod 13 has an axis $A_1$, and rod 14 has an axis $A_2$ (see FIG. 1A). The rods 13 and 14 have an upwardly-pointing bend (as viewed in FIG. 1) at a station 15 (hereinafter bend 15) that is located about one-third of the length of the rods from the yoke 18. The column 12 is initially prestressed by virtue of the bend 15. At the bend 15, the axes of the rods rotate through a predetermined angle $\beta$ to a new orientation identified as a $A_1'$ and $A_2'$. The angle $\beta$ is in the range of between 5° and 20° and is preferably about 15°, so that an included angle Δ measured about the bend 15 is preferably about 165°.

The bend 15 is more clearly shown in FIG. 2. The axis $A_1$, for example, represents the axis of the portion of the erector rod 13 lying between the bend 15 and the encasement 32.

The axis $A_1'$ represents the axis of the portion of the erector rod 13 lying between the bend 15 and the yoke 18.

The bend 15 causes the glans 2 to be raised upward (as viewed in FIG. 1) relative to the axis $A_1$. Because of bend 15, the column 12 lies below an imaginary straight line H that extends between the penis root 7 and the apex 5 of the corona 3. By virtue of the upward reorientation of the glans 2, vaginal contact with the erector is avoided and primarily restricted to the penis with initial contact involving the glans 2 and lower penile portion 6 (see FIG. 1).

Referring again to FIG. 1, the erector is shown as applied to a user. In the installed condition, the elastomeric tube 28 encircles the scrotum and is held in place by means of the engagement of the ring 31 with the button 29. The yoke 18 encircles the glans 2 and lies in the corona sulcus 8. The extremeties 21 and 22 of the yoke arms 19 and 20 respectively, terminate at their respective tips 21' and 22' in the vicinity of the urethra 4 and penile axis $A_3$, the extremities being slightly submerged into the glans 2 (see FIG. 1D). The thicknesses 17 and 17' (see FIG. 1B) of the yoke arms 19 and 20 are such that the yoke arms do not extend beyond the corona 3 of the glans 2.

The column 12 at the bend 15 contacts the superficial dorsal vein for controlling the flow of venial blood therein. The bend at the second ends 24 and 25 has a resilient and enlarged encasement 32 (shown in cross-sectional view in FIG. 1G) that also applies pressure to the superficial dorsal vein. The encasement 32 applies such pressure without causing pressure on the arterial vessels and corpora cavernosum urethra.

The erector may be considered dynamical in its operation because it automatically follows changes in the size of the penis when erection occurs or weakens. More specifically, as a result of erection, the penis expands such that the arms 19 and 20 of the yoke rotate relatively further apart. Such yoke arm rotation causes extremities 21 and 22 to rotate relatively further apart about a pivotal axis defined by the point of contact between tips 21' and 22'. The tips 21' and 22' remain in contact during the dynamic operation of the erector and roll upon one another in correspondence to rotation of extremities 21 and 22.

The rods 13 and 14 being capable of rotation relative to each other, rotate about their respective axes in response to separating forces applied to yoke arms 19 and 20. The resiliency of the encasement 32 and the elastomeric tube causes the rods 13 and 14 to return to a neutral or closed position upon the removal of such forces from the yoke arms.

As a result of penile erection, the yoke arms 19 and 20 rotate relatively further apart causing the corresponding second ends 24 and 25 to move relatively closer together. As a result of such movement, relatively increasing pressure is applied to the superficial dorsal vein due to the contact of bend 15 and the vein. The increasing pressure causes constriction of the veinal flow of blood through the superficial dorsal vein. Additionally, as the second ends 24 and 25 rotate relatively closer together, the elastomeric tube 28 is thereby stretched causing a corresponding increase in pressure applied by means of second ends 24 and 25, through encasement 32, to the superficial dorsal vein and the corpora cavernosa at the penis root 7. The increasing pressure, as applied by the bend 15 and the second ends 24 and 25 (pressure shown in FIG. 2 as being applied at points I and J respectively), constricts the return flow of blood from the corpora cavernosa thereby controlling erection. Due to the complementary relation of the rods 13 and 14, the aforementioned process is reversed during weakening of penile erection.

By virtue of the elasticity of the elastomeric tube 28, the erector 10 in response to penile erection is capable of movement along the body of the penis. During use of the erector, extremities 21 and 22 of the yoke arms 19 and 20 do not extend beyond the glans 2 and thus do not contact the frenulum of the female pudendum nor do they contact the lower region of the vaginal wall. By virtue of the fact that the arms 19 and 20 do not extend beyond the corona 3 and that the extremities 21 and 22 rest against each other normally at the opening of the urethra 4 (see FIG. 1D), the erector is not felt by a woman during coitus.

Additionally, since extremities 21 and 22 are in abutting relationship, tendency of one extremity to slide relative to the other is eliminated. Thus, the situation, characterizing some devices of the prior art, whereby one extremity projects beyond the other leading to the potential of serious injury to the female, is eliminated. The penile axis $A_3$ (not shown in FIG. 1) may be considered as being coaxial with the urethra and thus at the "geometrical" center of the penis. Since the point of contact of tips 21' and 22' are in the vicinity of the axis $A_3$ and the arms 19 and 20 do not extend beyond the glans corona 3, the yoke does not contact the vaginal walls.

The foregoing is more clearly understood and shown in FIG. 2. The line L represents the distance between the line H and a straight line projection N that is taken along the lower penile portion 6. The distance M represents the largest transverse distance between the rod axis $A_1'$ and the yoke arms 19 and 20. As shown in FIG. 2, the distance L is greater than the distance M and since vaginal contact is about the penis there is essentially no vaginal contact with the erector.

Referring now to FIG. 3, there is shown a substantially semispherical probe 33 secured to the arms 19 and 20 and adapted for defloration. The probe 33 maintains the arms 19 and 20 relatively stationary, and the probe has a semi-spherical head 34 that is oriented such that upon vaginal entrance the spherical surface of the head 34 is first to penetrate the hymen. Similarly, as in the case of the erector 10, the probe 33 does not touch the vaginal walls.

Referring now to FIG. 4, there is shown an erector 10 having a generally thimble-shaped probe 41 secured to the yoke arms 19 and 20. The probe 41 is mounted on compensators 37 and 38. The compensators 37 and 38 are for compensating instances of size disproportion between the penis and vagina, especially involving relatively large differences between penile and vaginal lengths. Compensators 37 and 38 extend from and form a part of yoke arms 19 and 20, the compensators being in axial alignment with the axes of the penis. The compensators 37 and 38 have substantially semicircular bends 39 and 40 respectively, the bends lying essentially in a plane normal to the axes of the compensators forming thereby a planar split ring. The split ring formed by the compensators provides a frame upon which is mounted the probe 41.

FIG. 5 is a cross-sectional view taken along lines 5—5 of FIG. 4. The split ring formed by bends 39 and 40 is encased in a central, annular ring portion 36 located at the base of a thimble-shaped probe 41. Extending about the central ring portion 36 is a thin circular elastic disk 42 having concentric rings 43. The rings 43 extend beyond the surface of the disk 42 a distance approximately equal to the thickness of the disk 42. The radial spacings between the concentric rings 43 are approximately equal, and the outer diameter of the disk 42 is in the range preferably from 1 to 2 inches. The probe 41 has a solid shell portion 44 and a hollow interior portion 47.

A plug 46 is insertable into the hollow interior portion 47. The plug is capable of providing a water-tight seal at the central ring portion 36. The hollow interior portion 47 may be filled with a fluid, typically warm water, for providing a feeling of comfort and naturalness for the female during the use of the erector. The plug 46 has a finger grip portion 46' to be gripped by the fingers of the user for insertion and removal of the plug 46 from the probe 41.

A plurality of elastic bristles 45 for cervical stimulation extend outwardly from the outer surface of the probe 41. Preferably the probe 41 has about five bristles 45. It will be understood, however, that the number of bristles is arbitrary and the number may vary according to design. The bristles may be any of a number of shapes such as, for example, cylindrical or conical. Preferably, the bristles extend approximately ½ inch beyond the outer surface of the shell portion 44.

A protective encasement such as rubber or latex encases the compensators 37 and 38. The probe 41 and the plug 46 are also formed of a rubber or latex material similar to that used for the sleeve 16.

The length of the compensators 37 and 38 depend upon the partners for which the use of the erector is intended, and is typically about 1½ inches. Compensators longer than 1½ inches may be linked together by any one of a number of conventional linking techniques such as the use of small rubber bands.

Referring now to FIG. 6, there is shown an erector formed as a surgical penile splint used for surgical procedures when a penis has to be fixed in a stretched position to the length of a full erection. Examples of such surgical procedures include remedying of penile fractures and the breakage of the corpora cavernosa. The erector, as shown in FIG. 6, is similar to that of the erector shown in FIG. 1 except for the provision of the square bend 49 located in the area in which the surgical operation is to be performed. The square bend 49 has two leg portions 52 and 53 extending essentially normal to the rods 13 and 14. An interconnecting leg 54 interconnects legs 52 and 53. The length of the legs 52 and 53 is selected to provide sufficient clearance for the use of surgical implements necessary for intended surgical procedures. The invention contemplates bends other than square, the shape of the bend being influenced by the procedure to be performed.

While the basic principle of this invention has been herein illustrated along with one embodiment, it will be appreciated by those skilled in the art that variations in the disclosed arangement both as to its details and as to the organization of such details may be made without departing from the spirit and scope thereof. Accordingly, it is intended that the foregoing disclosure and the showings made in the drawings will be considered only as illustrative of the principles of the invention and not construed in a limiting sense.

What is claimed is:

1. A prosthetic erector comprising:
an elongated rod means having first and second ends, a yoke coupled at the first end of the rod means, the yoke having first and second arms forming a pair of spaced apart, generally hooked-shaped arcuate arms adapted for encircling the glans of the penis around and in abutment with the corona sulcus, the extremities of the arms located in the vicinity of the opening at the penis urethra, a supporting arc portion at the second end of the rod means conforming to the contour of the pubic muscles, the rod means having an upward bend with respect to the longitudinal axis of the rod means located at a station about one-third of the length of the rod away from the first end, the bend initially stressing the rod means so that, when the arms support the weight of the penis, the rod means contacts the penis superficial dorsal vein for applying pressure thereto; and securement means at the second end of the rod means for securing the erector to the penis, said means formed from elastomeric material and adapted for securement around the penis scrotum at the root of the penis.

2. The erector of claim 1 wherein the elongated rod means comprises two rods each having an axis, the rods encased within a common sleeve, the rods being in substantially side-by-side relation, the rods being capable of rotation relative to each other about their respective axes.

3. The erector of claim 2 further comprising a thin filament wrapped around the two rods in a helical fashion for maintaining the rods in side-by-side relation.

4. The erector of claim 3 wherein the first end of each rod is coupled to a respective one of the arcuate arms and the second end of each rod is coupled to the securement means.

5. The erector of claim 4 wherein the second end of each rod has a bend, said second ends being separated thereby from each other at a predetermined angle, the second ends for contacting and applying pressure thereby to the penis superficial dorsal vein.

6. The erector of claim 5 wherein the securement means comprises elastomeric means coupled to the second end of each rod and adapted for securement around the scrotum at the root of the penis, the elastomeric means being capable of stretching and retracting in response to corresponding changes in erection of the penis, and wherein expansion of the glans of the penis causes the arms of the yoke to rotate relatively further apart causing the second ends of the rods to rotate relatively closer together stretching thereby the elastomeric means causing the second ends of the rods to exert relatively increasing pressure on the dorsal vein and the elastomeric means causing relatively increasing pressure on the corpora cavernosa without casing relatively increasing pressure on the arterial vessels and corpus cavernosum urethra.

7. The erector of claim 6 wherein the extremities of the yoke arms each have a tip, the tips being in abutting contact, the extremities being in mutual contact along a portion of their length, and upon rotation of the yoke arms relatively further apart, the extremities rotate correspondingly relatively further apart, the tips remaining in abutting contact as the extremities rotate.

8. The erector of claim 7 wherein the extremities rotate about a pivotal axis, the pivotal axis located essentially at the point of contact between the tips, the tips rolling one upon the other in correspondence to the rotation of the extremities.

9. The erector of claim 6 wherein the elastomeric means comprises:
an elastomeric tube, the tube having first and second ends, the tube coupled at the first end to a respective second end of one rod; and
locking means coupled to the second end of the tube and the second end of the other rod for detachable engagement of the second ends of the tube and said other rod.

10. The erector of claim 9 wherein the elastic encasement encasing the arcuate arms located in the corona sulcus does not extend beyond the perimeter of the corona of the glans of the penis.

11. The erector of claim 9 wherein the extremities of each arm of the yoke are capable of being partially submerged within the glans of the penis.

12. The erector of claim 9 wherein the elastomeric tube is hollow, the second end of one rod being capable of insertion within said hollow tube for adjusting the length of the tube between such second end of one rod and the second end of the elastomeric tube; and
clamping ring means for clamping the elastomeric tube to such second end of one rod at the selected adjusted length.

13. The erector of claim 9 further comprising first and second substantially rigid compensators, each compensator having an axis, the first compensator being coupled at one end to one of the arcuate arms and the second compensator being coupled at one end to the other arcuate arm, the other ends of the compensators having substantially semi-circular bends essentially normal to the axes of the compensators forming thereby a planar split ring; and
a hollow resilient thimble-shaped probe having an open end, the probe mounted on the split ring, the probe having a plurality of resilient projections at the outer surface of the probe.

14. The erector of claim 13 wherein the probe is mounted at its open end on the split ring, the probe further comprising plug means adapted for providing a water-tight seal at the open end of the probe.

15. The erector of claim 9 wherein the elastomeric tube is coupled to one supporting arc at the extremity thereof and the locking means is coupled to the other supporting arc at the extremity thereof.

16. The erector of claim 1 further comprising defloration means comprising a substantially spherical probe, the probe mounted to the erector at the extremity of the arcuate arms, the probe maintaining the extremity of the arcuate arms relatively fixed, the probe oriented such that upon vaginal entrance the spherical surface of the probe first penetrates the hymen.

17. The erector of claim 1 wherein the bend comprises a predetermined included angle in the range of about 165° to 175°.

18. A prosthetic erector comprising: an elongated rod means comprising two upwardly with respect to the longitudinal axis of the rod means bent rods, each rod having first and second ends, each rod having an axis, the rods being in substantially side-by-side relation, the rods being capable of rotation relative to each other about their respective axes through a predetermined angle;
a yoke coupled to the first ends of the rods, the yoke having a pair of spaced apart arms wherein the first end of each rod is coupled to a respective one of the arms, the yoke adapted for encircling the penis glans, the yoke arms being in contact with the penis corona along the corona sulcus, the extremities of the yoke arms having a tip, the tips being in abutting contact, the extremities being in mutual contact along a portion of their length, and wherein expansion of the glans causes the arms of the yoke to rotate relatively further apart, the extremities correspondingly rotating relatively further apart, the tips remaining in abutting contact as the extremities rotate;
a supporting arc portion at the second end of each rod, such arc portions conforming to the contour of the pubic muscles; and
securement means, coupled to the arc portions for securing the erector to the penis, said securement means adapted for securement around the scrotum.

19. A prosthetic device for inducing erection of a penis comprising:
an elongate rod means having a root end and a tip end for attachment along the elongate axis of a penis on its dorsal side;
the root end of the rod means being connected to a pair of curved arms contoured to conform to the upper portion of the male pubic muscles;
securement means coupled to the arms for encircling the penis scrotum, so that, when secured, the connection of the curved arms to the root end of the rod means disposes the rod means in an erect orientation roughly perpendicular away from the male torso;
the tip end of the rod means being coupled to a yoke which has a pair of arcuate members contoured for supporting the glans of the penis around and in abutment with the corona sulcus;
such members extending from beneath the glans beyond the corona sulcus to terminate in mutual side-by-side contact along an end portion in the vicinity of the opening of the penis urethra;
the rod means being bent upwardly with respect to the longitudinal axis from a bend toward the tip end, the bend being located about two-thirds of the length of the rod means from the root end, whereby, in response to support of the weight of the penis glans by the arcuate members, the rod means applies pressure to the penis superficial dorsal vein, from the root end of the rod means to the bend, for inducing erection of the penis.

20. A prosthetic device according to claim 19 wherein the tip end of the rod means is bent sufficiently upwardly so that, in use, the rod means is disposed below the uppermost size extent of the penis, and the arcuate members are disposed above the lowermost size extent of the penis.

21. A prosthetic device according to claim 20 wherein the members are capable of rotation relatively further apart while remaining in mutual contact along the end portion.

22. A prosthetic device according to claim 21 wherein the elongate rod means comprises two elongate rods in side-by-side relation encased in a common sleeve, the rods being capable of rotation relative to each other about their respective axes.

23. A prosthetic device according to claim 22 wherein at least one of the rods is integrally formed at its root end with a respective one of the curved arms, such rod being integrally formed at its tip end with a respective one of the arcuate members.

24. A prosthetic device according to claim 23 wherein the securement means comprises a resilient structure capable of stretching and retracting in response to corresponding changes in erection of the penis, and wherein expansion of the glans of the penis causes the members to rotate relatively further apart whereby the arms rotate relatively further apart in response, stretching thereby the resilient structure causing the rod means to exert additional pressure on the dorsal vein and the corpora cavernosa of the penis.

25. The prosthetic device according to claim 24 wherein such additional pressure is exerted on the dorsal vein and the corpora cavernosa essentially without increasing pressure on the arterial vessels of the penis.

26. A prosthetic device according to claim 21 wherein the members apply pressure to the corona sulcus during such rotation.

27. The prosthetic device according to claim 19 wherein the arcuate members are capable of being partially submerged within the glans of the penis.

28. A prosthetic device for inducing erection of a penis comprising:
an elongate rod means having a root end and a tip end for attachment along the elongate axis of a penis on its dorsal side;
the root end of the rod means being connected to a pair of curved arms contoured to conform to the upper portion of the male pubic muscles;
securement means coupled to the arms for encircling the penis scrotum, so that, when secured, the connection of the curved arms to the root end of the rod means disposes the rod means in an erect orientation roughly perpendicular away from the male torso;
the tip end of the rod means being coupled to a yoke which has a pair of arcuate members contoured for supporting the glans of the penis around and in abutment with the corona sulcus;
such members extending from beneath the glans beyond the corona sulcus to terminate in mutual side-by-side contact along an end portion in the vicinity of the opening of the penis urethra; and
the rod means being bent upwardly with respect to the longitudinal axis for lifting the axis of the glans relative to the axis of the remainder of the penis.

29. A prosthetic device according to claim 28 wherein the rod means is bent sufficiently upwardly so that the rod means is disposed below the uppermost size extent of the penis, and the arcuate members are disposed above the lowermost size extent of the penis.

30. A prosthetic device for inducing erection of a penis comprising:
an elongate rod means having a root end and a tip end for attachment along the elongate axis of a penis on its dorsal side;
the root end of the rod means being connected to a pair of curved arms contoured to conform to the upper portion of the male pubic muscles;
securement means coupled to the arms for encircling the penis scrotum, so that, when secured, the connection of the curved arms to the root end of the rod means disposes the rod means in an erect orientation roughly perpendicular away from the male torso;
the tip end of the rod means being coupled to a yoke which has a pair of arcuate members contoured for supporting the glans of the penis around and in abutment with the corona sulcus;
such members extending from beneath the glans beyond the corona sulcus to terminate in mutual side-by-side contact along an end portion in the vicinity of the opening of the penis urethra; and
the rod means being upwardly with respect to the longitudinal axis concave so that when the arcuate members support the penis glans, a major portion of the length of the rod means applies pressure to the penis superficial dorsal vein for inducing erection of the penis.

31. A method for inducing erection of a penis comprising:
securing a prosthetic device around the root of the penis so that an elongate member of the device projects roughly perpendicularly away from the male torso in contact with the shaft of the penis just above the superficial dorsal vein;
supporting the weight of the glans of the penis through the prosthetic device; and
bending the glans upwardly longitudinal axis of the relative to the shaft to convert the weight of the glans into pressure applied by the member to the superficial dorsal vein to constrict the flow of blood from the penis thereby to induce erection of the penis.

* * * * *

UNITED STATES PATENT AND TRADEMARK OFFICE
CERTIFICATE OF CORRECTION

PATENT NO. : 4,362,152
DATED : December 7, 1982
INVENTOR(S) : Gorokhovsky et al

It is certified that error appears in the above—identified patent and that said Letters Patent is hereby corrected as shown below:

On the front cover, delete "et al" after Gorokhovsky. [76] delete "inventors" and insert -- Inventor --; delete "Grigory Fradkin, 1230 N. Sweetzer Ave., #313, Los Angeles, Calif. 90069".

Column 3, line 63, delete "electric" and insert -- elastic --. Column 8, line 61, delete "casing" and insert -- causing --. Column 9, lines 64 and 65, after "two" delete the phrase "upwardly with respect to the longitudinal axis of the rod means bent rods, each rods" and insert -- rods, each rod being upwardly bent with respect to the longitudinal axis of the rod means, and --. Column 12, line 31, after "upwardly" insert -- concave --. Column 12, line 32, delete "concave". Column 12, line 46, delete "longitudinal axis of the". Column 12, line 47, after the words "to the" insert -- longitudinal axis of the --.

Signed and Sealed this

Twenty-sixth Day of April 1983

[SEAL]

Attest:

GERALD J. MOSSINGHOFF

Attesting Officer    Commissioner of Patents and Trademarks